US008080503B2

(12) United States Patent
Salvador et al.

(10) Patent No.: US 8,080,503 B2
(45) Date of Patent: Dec. 20, 2011

(54) CLEANSING BAR COMPOSITIONS COMPRISING A HIGH LEVEL OF WATER

(75) Inventors: Charlie Reyes Salvador, Beijing (CN); Chunpeng Jiang, Beijing (CN); Lihuan Wu, Beijing (CN); Toshihiko Okano, Kobe (JP); Yan Zhang, Beijing (CN); Pamela Angeles Diocos, Beijing (CN); Daniel Samuel Samaco Perez, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/607,667

(22) Filed: Dec. 1, 2006

(65) Prior Publication Data

US 2007/0155639 A1 Jul. 5, 2007

Related U.S. Application Data

(63) Continuation-in-part of application No. 11/453,767, filed on Jun. 15, 2006.

(60) Provisional application No. 60/692,027, filed on Jun. 18, 2005, provisional application No. 60/811,544, filed on Jun. 6, 2006.

(51) Int. Cl.
*A61K 7/50* (2006.01)

(52) U.S. Cl. ........ 510/141; 510/150; 510/152; 510/153; 510/155; 510/156

(58) Field of Classification Search ........................ None
See application file for complete search history.

(56) References Cited

U.S. PATENT DOCUMENTS 1,475,663 A 11/1923 Tseng
2,438,091 A 3/1948 Lynch
2,438,169 A 3/1948 Hoyt
2,528,378 A 10/1950 Mannheimer
2,658,072 A 11/1953 Kosmin
2,982,735 A 5/1961 Blinka et al.
3,179,596 A 4/1965 Farrar et al.
3,224,976 A 12/1965 Farrar et al.
3,226,329 A 12/1965 MacMillan
3,247,121 A 4/1966 Henricks
3,494,869 A 2/1970 Armstrong
3,824,189 A 7/1974 Borrello
3,835,058 A 9/1974 White
4,097,407 A 6/1978 Ady
4,297,230 A 10/1981 Rasser
4,396,521 A 8/1983 Borrello
4,673,525 A 6/1987 Small et al.
4,808,322 A 2/1989 McLaughlin
4,812,253 A 3/1989 Small et al.
4,820,447 A 4/1989 Medcalf et al.
4,851,147 A 7/1989 Esposito et al.
4,874,538 A * 10/1989 Dawson et al. ............... 510/147
4,946,618 A 8/1990 Knochel et al.
4,963,284 A 10/1990 Novakovic et al.
4,985,170 A 1/1991 Dawson et al.
5,002,685 A 3/1991 Chambers et al.
5,057,311 A 10/1991 Kamegai et al.
5,057,359 A 10/1991 Merdem et al.
5,064,555 A 11/1991 Medcalf et al.
5,076,953 A 12/1991 Jordan et al.
5,096,608 A 3/1992 Small et al.
5,202,048 A 4/1993 Bartolo et al.
5,264,144 A 11/1993 Moroney et al.
5,340,492 A 8/1994 Kacher et al.
5,387,362 A 2/1995 Tollens et al.
5,425,892 A 6/1995 Taneri et al.
5,631,215 A 5/1997 Kinsman
5,683,973 A 11/1997 Post et al.
5,703,026 A 12/1997 Setser et al.
5,723,420 A 3/1998 Wei et al.
5,965,501 A 10/1999 Rattinger et al.
6,057,275 A 5/2000 Fair et al.
6,242,397 B1 6/2001 Milio et al.
6,310,016 B1 10/2001 Behal et al.
6,336,553 B1 1/2002 Gordon
6,440,908 B2 8/2002 Racheria
6,488,943 B1 12/2002 Beerse et al.
6,562,772 B1 5/2003 Maurin et al.
6,841,524 B1 1/2005 Patel et al.

(Continued)

FOREIGN PATENT DOCUMENTS

EP 0155915 A2 9/1985

(Continued)

OTHER PUBLICATIONS

Office Action pertaining to U.S. Appl. No. 11/453,767 dated Jun. 25, 2008.
Office Action pertaining to U.S. Appl. No. 11/453,767 dated Mar. 19, 2009.
Advisory Action pertaining to U.S. Appl. No. 11/453,767 dated May 26, 2009.
Office Action pertaining to U.S. Appl. No. 11/453,767 dated Aug. 4, 2009.
Office Action pertaining to U.S. Appl. No. 11/453,767 dated Jun. 16, 2010.
International Search Report, PCT/US2007/024719, dated Apr. 4, 2008 (6 pages).
J. A. Radley, Industrial Uses of Starch and Its Derivatives, 1976, Applied Science Publishers Ltd, London, GB (2 pages).

(Continued)

*Primary Examiner* — Necholus Ogden, Jr.
(74) *Attorney, Agent, or Firm* — Mark A. Charles; Jason J. Camp

(57) ABSTRACT

Cleansing bar compositions having high water content comprise: (a) at least about 15%, by weight of the composition, of water; (b) from about 40% to about 84%, by weight of the composition, of soap; and (c) from about 1% to about 15%, by weight of the composition, of inorganic salt. The bar compositions further comprise a component selected from the group consisting of carbohydrate structurant, humectant, free fatty acid, synthetic surfactants, and mixtures thereof. The bar compositions preferably have a Water Activity ("Aw") of less than about 0.95, preferably less than about 0.90, and more preferably less than about 0.85. The bar compositions are preferably manufactured by a milling process.

19 Claims, No Drawings

U.S. PATENT DOCUMENTS

| | | | |
|---|---|---|---|
| 6,849,585 | B1 | 2/2005 | Farrell et al. |
| 6,852,681 | B1 | 2/2005 | Kerschner et al. |
| 6,949,493 | B1 | 9/2005 | Zhang et al. |
| 7,045,491 | B2 | 5/2006 | Hourigan |
| 2001/0046950 | A1 | 11/2001 | Agrawal et al. |
| 2005/0003975 | A1 | 1/2005 | Browne et al. |
| 2005/0069861 | A1 | 3/2005 | Zimmermann et al. |
| 2005/0192192 | A1 | 9/2005 | Bouzas et al. |
| 2005/0227886 | A1 | 10/2005 | Patel et al. |
| 2006/0201115 | A1 | 9/2006 | Van Gordon et al. |
| 2006/0287206 | A1 | 12/2006 | Nadakatti et al. |
| 2007/0021314 | A1 | 1/2007 | Salvador et al. |
| 2007/0155639 | A1 | 7/2007 | Salvador et al. |
| 2008/0020959 | A1 | 1/2008 | Salvador et al. |
| 2009/0143267 | A1 | 6/2009 | Zhang et al. |

FOREIGN PATENT DOCUMENTS

| | | | |
|---|---|---|---|
| EP | 0 251 410 | A1 | 1/1988 |
| EP | 0 507 559 | B1 | 7/1995 |
| EP | 0665915 | B1 | 4/1997 |
| FR | 895204 | | 1/1945 |
| GB | 2 271 120 | A | 4/1994 |
| JP | 45007977 | B | 3/1970 |
| KR | 4072158 | A | 8/2004 |
| RO | 58594 | A2 | 9/1975 |
| WO | WO-92/05241 | A1 | 4/1992 |
| WO | WO-93/02174 | A1 | 2/1993 |
| WO | WO-96/35772 | A1 | 11/1996 |
| WO | WO-97/22684 | A1 | 6/1997 |
| WO | WO 98/54285 | | 12/1998 |
| WO | WO 99/50382 | | 10/1999 |
| WO | WO-02/086043 | A1 | 10/2002 |
| WO | WO-03/068901 | A1 | 8/2003 |
| WO | WO-2006/138738 | A1 | 12/2006 |

OTHER PUBLICATIONS

Chemical Abstracts, vol. 73, No. 10, Sep. 7, 1970, p. 83, abstract No. 46963b, Columbus, Ohio, US; & JP-A-70 07 977 (Lion Fat and Oil Co.) Mar. 20, 1970.

Chemical Abstracts, vol. 88, No. 24, Jun. 24, 1978, p. 95, abstract No. 171825u, Columbus, Ohio, US; & RO-A-58 594 (Combinatul De Piele Si Incaltaminte "Clujana") Apr. 8, 1971.

J. A. Radley, Industrial Uses of Starch and Its Derivatives, 1976, Applied Science Publishers Ltd, London, GB (2 pages).

* cited by examiner

CLEANSING BAR COMPOSITIONS COMPRISING A HIGH LEVEL OF WATER

CROSS REFERENCE TO RELATED APPLICATIONS

This application is a continuation-in-part of U.S. application Ser. No. 11/453,767 filed on Jun. 15, 2006, which claims the benefit of U.S. Provisional Application Ser. No. 60/692,027 filed on Jun. 18, 2005 and U.S. Provisional Application Ser. No. 60/811,544 filed on Jun. 6, 2006.

FIELD OF THE INVENTION

The present invention relates to bar compositions for cleansing skin comprising a high level of water.

BACKGROUND OF THE INVENTION

Bar soaps remain a popular product form for cleansing skin. Those skilled in the art use the term soap to designate the reaction product of a carboxylic acid with a base, typically a metal hydroxide or carbonate. The resulting salt has both a polar hydrophilic end and a non-polar lipophilic end which facilitates the removal of oils and other non-polar materials from the skin or other surface in the presence of water.

Bar soaps are customarily prepared either by framing/casting or by milling/plodding. Framed or cast soaps are typically prepared by reacting an appropriate fat, oil or carboxylic acid with a base in the presence of water to form soap, pouring the molten soap containing about 30% water into a frame or a mold, allowing the soap to cool and harden, and removing the soap having about 20% to 25% water by weight in a bar form. The fatty acid can be obtained from a fat, such as tallow or lard, from an oil, such as coconut oil, palm oil, palm kernel oil, or olive oil, or from combinations of fats and oils. Fats and oils are comprised in substantial part of glycerides of varying chain lengths, which are esters of glycerol (glycerin) and fatty acids. Under alkaline conditions, and in the presence of heat, the glycerides constituting the fats and oils break down to form fatty acid salts, also known as soaps, and glycerin.

Milled/plodded soap bars are produced by subjecting the neutralized soap to various finishing steps which alter the crystalline matrix of the soap from the omega phase, as formed in framed/cast soap bars, to the beta phase. A more detailed discussion may be found in Bailey's Industrial Oil And Fat Products, 4th ed., Vol. 1, p. 558 et seq. (1979). Prior to conversion the soap is first dried from a moisture level of approximately 30% to a level in the range of about 10% to about 14%. Next, the dried soap is generally sent to a simple paddle-type mixer where a variety of additives can be introduced. From this mixer the soap is then sent either directly to a refiner or optionally to a three-roll mill and then to the refiner. Both the refiner and the mill subject the soap to compression and an intense shearing action which tend to orient the soap crystals and convert the soap largely to the beta-phase. After refining, the soap is compressed into a dense, coherent form in a plodding operation which forms solid portions which are suitable for stamping into bars.

The drying step is typically necessary to remove the "gummy" texture and excessive pliability of the soap mass which exist typically at higher moisture levels. In the production of milled/plodded bars, drying to from about 10% to about 14% moisture is necessary to permit the soap mass to be processed through the finishing equipment. Drying on a commercial basis is achieved by several different methods. One procedure employs a water-chilled roll in combination with a second feed roll to spread molten, neutralized soap into a thin, uniform layer. The cooled soap is then scraped from the roll to form chips and dried to a specific moisture level in a tunnel dryer. Soap chips already having a low moisture level (about 10% to 11%) are further dried by repeatedly conducting the chips through close-set water cooled steel rolls (i.e., three-roll mill) in the procedure known as milling described above. A relatively modern technique for the drying of soap is known as spray drying. This process directs molten soap to the top of a tower via spray nozzles. The sprayed soap hardens and then dries in the presence of a current of heated air. Vacuum may be applied to facilitate the removal of water.

It is desirable to create a bar composition having high water content to allow for formulation and process efficiency. However, a problem with high water content bar compositions is that it can be difficult to maintain the high water content in the finished bar composition. There thus remains a desire to develop a high water content bar composition in which the relatively high water content is maintained in the finished bar composition and the bar composition is stable and suitable for consumer use.

SUMMARY OF THE INVENTION

The present invention relates to bar compositions comprising: (a) at least about 15%, by weight of the composition, of water; (b) from about 40% to about 84%, by weight of the composition, of soap; and (c) from about 1% to about 15%, by weight of the composition, of inorganic salt. The inorganic salt helps to maintain the relatively high level of water in the bar composition. Preferred inorganic salts include sodium tripolyphosphate, magnesium salts, and/or tetrasodium pyrophosphate. The bar composition preferably further comprises a carbohydrate structurant, such as raw starch or pregelatinized starch, which can tend to further aid in maintaining the relatively high level of water in the bar composition. Humectants can optionally be included in the present bar compositions to improve bar hardness. Free fatty acid can optionally be included in the bar composition to provide enhanced skin feel benefits. Synthetic surfactants can be optionally added to the bar composition to provide enhanced lathering characteristics of the composition. The present bar compositions will preferably have a Water Activity ("Aw") of less than about 0.95, preferably less than about 0.90, and more preferably less than about 0.85. The Water Activity ("Aw") is a measure reflecting how well the water level is maintained in the finished bar composition.

The bar composition is preferably produced by a milling process. The present invention thus further relates to a process of manufacturing a bar composition comprising a high level of water according to a milling process.

DETAILED DESCRIPTION OF THE INVENTION

Water

The bar compositions of the present invention comprise at least about 15%, more preferably at least about 20%, and more preferably at least about 25%, by weight of the composition, of water. The level of water can be still higher, e.g. 30%, 35%, or even 40%, but is typically not greater than about 60%, preferably not greater than about 55%, and more preferably not greater than about 50%, by weight of the bar composition.

It should be understood that an amount of water will be lost, i.e. evaporated, during the process of making the bar composition. Also, once the finished product is made, water can be further lost from the bar composition due to water evaporation, water being absorbed by surrounding packaging (e.g. a cardboard carton), and the like.

It can be important to incorporate in the bar composition materials that tend to bind the water such that it is maintained in the bar composition. Such materials include the inorganic salts, humectants, and/or the carbohydrate structurants described herein. Such materials can have an affect on the "water activity" in the bar composition. Water Activity ("Aw"), and a method for measuring it, is described in more detail hereinbelow. The present bar compositions will preferably exhibit a Water Activity ("Aw") of less than about 0.95, preferably less than about 0.9, more preferably less than about 0.85, and more preferably less than about 0.80, as measured by the "Water Activity Test Method" described hereinbelow.

Soap

The bar compositions of the present invention will typically comprise from about 40% to about 84%, preferably from about 45% to about 75%, and more preferably from about 50% to about 65%, by weight of the composition, of soap. The term "soap" is used herein in its popular sense, i.e., the alkali metal or alkanol ammonium salts of alkane- or alkene monocarboxylic acids. Sodium, magnesium, potassium, calcium, mono-, di- and tri-ethanol ammonium cations, or combinations thereof, are suitable for purposes of the present invention. In general, sodium soaps are used in the compositions of this invention, but from about 1% to about 25% of the soap may be ammonium, potassium, magnesium, calcium or a mixture of these soaps. The soaps useful herein are the well known alkali metal salts of alkanoic or alkenoic acids having about 12 to 22 carbon atoms, preferably about 12 to about 18 carbon atoms. They may also be described as alkali metal carboxylates of alkyl or alkene hydrocarbons having about 12 to about 22 carbon atoms.

Soaps having the fatty acid distribution of coconut oil may provide the lower end of the broad molecular weight range. Those soaps having the fatty acid distribution of peanut or rapeseed oil, or their hydrogenated derivatives, may provide the upper end of the broad molecular weight range.

It can be preferred to use soaps having the fatty acid distribution of tallow, and vegetable oil. More preferably the vegetable oil is selected from the group consisting of palm oil, coconut oil, palm kernel oil, palm oil stearine, and hydrogenated rice bran oil, or mixtures thereof, since these are among the more readily available fats. Especially preferred are palm oil stearine, palm kernel oil, and/or coconut oil. The proportion of fatty acids having at least 12 carbon atoms in coconut oil soap is about 85%. This proportion will be greater when mixtures of coconut oil and fats such as tallow, palm oil, or non-tropical nut oils or fats are used, wherein the principle chain lengths are C16 and higher.

A preferred soap is sodium soap having a mixture of from about 50% to about 80%, more preferably from about 35% to about 40%, tallow; from 0% to about 60%, more preferably from 0% to about 50%, palm stearine; from 0% to about 40%, more preferably from 0% to about 35%, palm oil; and from about 10% to about 35%, more preferably from about 15% to about 30%, palm kernel oil or coconut oil.

The soaps may contain unsaturation in accordance with commercially acceptable standards. Excessive unsaturation is normally avoided.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric (C12), myristic (C14), palmitic (C16), or stearic (C18) acids with an alkali metal hydroxide or carbonate.

In one embodiment, the bar composition will comprise soap made by a continuous soap manufacturing process. The soap, which comprises approximately 30% water, is then processed into soap noodles via a vacuum flash drying process. The soap noodles preferably comprise from about 70% to about 85% anhydrous soap and at least about 15% water. These percentage amounts are by weight of the soap noodles. The soap noodles are then utilized in a milling process to make the finished bar composition as described below.

Inorganic Salts

Inorganic salts can be utilized in the present bar compositions to help in maintaining the relatively high water content of the present compositions. The inorganic salts help to bind the water in the bar composition thereby preventing water loss by evaporation or other means. The present bar compositions comprise from about 1% to about 15%, preferably from about 2% to about 12%, and more preferably from about 2.5% to about 10.5%, by weight of the composition, of inorganic salt. Higher levels of inorganic salts are generally preferred, as higher inorganic salt levels tend to reduce Water Activity ("Aw") of water in the present compositions. Suitable inorganic salts include magnesium nitrate, trimagnesium phosphate, calcium chloride, sodium carbonate, sodium aluminum sulfate, disodium phosphate, sodium polymetaphosphate, sodium magnesium succinate, sodium tripolyphosphate, aluminum sulfate, aluminum chloride, aluminum chlorohydrate, aluminum-zirconium trichlorohydrate, aluminum-zirconium trichlorohydrate glycine complex, zinc sulfate, ammonium chloride, ammonium phosphate, calcium acetate, calcium nitrate, calcium phosphate, calcium sulfate, ferric sulfate, magnesium chloride, magnesium sulfate, and the like. Preferred inorganic salts include sodium tripolyphosphate, magnesium salts (such as magnesium sulfate), and/or tetrasodium pyrophosphate. Magnesium salts, when used as an ingredient in the present bar compositions comprising soap, tend to be converted to magnesium soap in the finished product. Sodium tripolyphosphate, magnesium salts (and as a result magnesium soap), and/or tetrasodium pyrophosphate are preferred in the present compositions as they are believed to contribute to decreasing the Water Activity ("Aw") of the water in the present compositions. Sodium tripolyphosphate is also preferred as it can tend to promote the generation of lather as the bar composition is used by a consumer for cleansing skin.

Carbohydrate Structurants

Carbohyrate structurants can optionally, but preferably, be included as ingredients in the present bar compositions. Carbohydrate structurants tend to assist in maintaining the relatively high level of water in the present compositions. Suitable carbohydrate structurants as ingredients in the present compositions include raw starch (corn, rice, potato, wheat, and the like), pregelatinzed starch, carboxymethyl cellulose, stabylene, carbopol, carregeenan, xanthan gum, polyethylene glycol, polyethylene oxide, and the like. Preferred carbohydrate structurants include raw starch and/or pregelatinized starch.

A preferred carbohydrate structurant for incorporating in a bar composition is starch. The starch can be either raw starch or it can be pregelatinized starch. Alternatively, raw starch can be used and modified during the process of making the bar composition such that the starch becomes gelatinized, either partially or fully gelatinized. Pregelatinized starch is starch that has been gelatinized before added as an ingredient in the present bar compositions. Gelatinized starch, either partially or fully gelatinized starch, can be preferred for providing enhanced skin feel benefits, such as providing a soft and smooth skin feel. A preferred pregelatinized starch for use as an ingredient in the present compositions is PREGEL-A M 0300 commercially available from Tianjin Tingfung Starch Development Co., Ltd. of Tianjin, China.

The level of carbohydrate structurant in the present compositions is typically from about 1% to about 20%, preferably from about 2% to about 17%, and more preferably from about 4% to about 15%, by weight of the composition.

Humectant

The compositions of the present invention can optionally further comprise humectant. The humectants herein are generally selected from the group consisting of polyhydric alcohols, water soluble alkoxylated nonionic polymers, and mixtures thereof. The humectants herein are preferably used at levels by weight of the composition of from about 0.1% to about 20%, more preferably from about 0.5% to about 15%, and more preferably from about 1% to about 10%.

Humectants, such as glycerin, can result from the production of anhydrous soap of the present invention by removing less glycerin as by product after saponification. The humectant can thus be a component of the soap noodle used in preparation of the present compositions. As a product of the anhydrous soap reaction, the level of humectant in the soap noodle is typically no more than about 1%, by weight of the soap noodle.

In one embodiment of the present invention, it can be advantageous to purposely add additional humectant, such as glycerin, to the composition. The additional humectant can be added to the soap noodle used in preparation of the present compositions. The additional humectant can be added either before the drying process of the neat soap containing about 30% water, or after the drying process. The total level of humectant in this case will typically be at least about 1%, preferably at least about 2%, more preferably at least about 3%, by weight of the composition. Incorporating additional humectant into the present high moisture bar compositions can result in a number of benefits such as improvement in hardness of the bar composition, decreased Water Activity of the bar composition, and lowering the weight loss rate of the bar composition over time due to water evaporation.

Polyhydric alcohols useful herein include glycerin, sorbitol, propylene glycol, butylene glycol, hexylene glycol, ethoxylated glucose, 1, 2-hexane diol, hexanetriol, dipropylene glycol, erythritol, trehalose, diglycerin, xylitol, maltitol, maltose, glucose, fructose, sodium chondroitin sultate, sodium hyaluronate, sodium adenosin phosphate, sodium lactate, pyrrolidone carbonate, glucosamine, cyclodextrin, and mixtures thereof.

Water soluble alkoxylated nonionic polymers useful herein include polyethylene glycols and polypropylene glycols having a molecular weight of up to about 1000 such as those with CTFA names PEG-200, PEG-400, PEG-600, PEG-1000, and mixtures thereof. Commercially available humectants herein include: glycerin with tradenames STAR and SUPEROL available from The Procter & Gamble Company, CRODEROL GA7000 available from Croda Universal Ltd., PRECERIN series available from Unichema, and a same tradename as the chemical name available from NOF; propylene glycol with tradename LEXOL PG-865/855 available from Inolex, 1,2-PROPYLENE GLYCOL USP available from BASF; sorbitol with tradenames LIPONIC series available from Lipo, SORBO, ALEX, A-625, and A-641 available from ICI, and UNISWEET 70, UNISWEET CONC available from UPI; dipropylene glycol with the same tradename available from BASF; diglycerin with tradename DIGLYCEROL available from Solvay GmbH; xylitol with the same tradename available from Kyowa and Eizai; maltitol with tradename MALBIT available from Hayashibara, sodium chondroitin sulfate with the same tradename available from Freeman and Bioiberica, and with tradename ATOMERGIC SODIUM CHONDROITIN SULFATE available from Atomergic Chemetals; sodium hyaluronate with tradenames ACTIMOIST available from Active Organics, AVIAN SODIUM HYALURONATE series available from Intergen, HYALURONIC ACID Na available from Ichimaru Pharcos; sodium adenosin phophate with the same tradename available from Asahikasei, Kyowa, and Daiichi Seiyaku; sodium lactate with the same tradename available from Merck, Wako, and Showa Kako, cyclodextrin with tradenames CAVITRON available from American Maize, RHODOCAP series available from Rhone-Poulenc, and DEXPEARL available from Tomen; and polyethylene glycols with the tradename CARBOWAX series available from Union Carbide.

Free Fatty Acid

Free fatty acid can optionally be added to the present bar compositions, typically at a level of from about 0.01% to about 10%, by weight of the composition. Free fatty acids can be incorporated in the present compositions to provide enhance skin feel benefits, such as softer and smoother feeling skin. Suitable free fatty acids include tallow, coconut, palm and palm kernel fatty acids. A preferred free fatty acid added as an ingredient in the present bar compositions is a high lauric fatty acid, such as palm kernel fatty acid or coconut fatty acid. Other fatty acids can be employed although the low melting point fatty acids, such as lauric acid, can be preferred for ease of processing. Preferred levels of free fatty acid added to the present bar compositions are from about 0.5% to about 2%, most preferably from about 0.75% to about 1.5%, by weight of the composition.

Synthetic Surfactant

Synthetic surfactants can be optionally utilized in the present bar compositions to further improve the lathering properties of the bar soap during use. The synthetic surfactants useful in this invention include anionic, amphoteric, nonionic, zwitterionic, and cationic surfactants. Synthetic surfactants are typically incorporated in the present compositions at a level of from about 0.1% to about 20%, preferably from about 0.5% to about 10%, and more preferably from about 0.75% to about 5%, by weight of the composition.

Examples of anionic surfactants include but are not limited to alkyl sulfates, anionic acyl sarcosinates, methyl acyl taurates, N-acyl glutamates, acyl isethionates, alkyl ether sulfates, alkyl sulfosuccinates, alkyl phosphate esters, ethoxylated alkyl phosphate esters, trideceth sulfates, protein condensates, mixtures of ethoxylated alkyl sulfates and the like. Alkyl chains for these surfactants are C8-22, preferably C10-18 and, more preferably, C12-14 alkyls.

Zwitterionic surfactants can be exemplified by those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, for example, carboxy, sulfonate, sulfate, phosphate, or phosphonate. Examples include: 4-[N,N-di(2-hydroxyethyl)-N-octadecylammonio]-butane-1-carboxylate; 5-[S-3-hydroxypropyl-S-hexadecylsulfonio]-3 hydroxypentane-1-sulfate; 3-[P,P-P-diethyl-P 3,6,9 trioxatetradecyl-phosphonio]-2-hydroxypropane-1-phosphate; 3-[N,N-dipropyl-N-3-dodecoxy-2-hydroxypropylammonio]-propane-1-phosphonate;3-(N,N-di-methyl-N-hexadecylammonio)propane-1-sulfonate; 3-(N,N-dimethyl- N-hexadecylammonio)-2-hydroxypropane-1-sulfonate; 4-(N,N-di(2-hydroxyethyl)-N-(2 hydroxydodecyl)ammonio]-butane-1-carboxylate; 3-[S-ethyl-S-(3-dodecoxy-2-hydroxypropyl)sulfonio]-propane-1-phosphate; 3-(P,P-dimethyl-P-dodecylphosphonio)-propane-1-phosphonate; and 5-[N,N-di(3-hydroxypropyl)-N-hexadecylammonio]-2-hydroxy-pentane-1-sulfate.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate; N-alkyltaurines, such as the one prepared by reacting dodecylamine with sodium isethionate according to the teaching of U.S. Pat. No. 2,658,072; N-higher alkyl aspartic acids, such as those produced according to the teaching of U.S. Pat. No. 2,438,091; and the products sold under the trade name "Miranol" and described in U.S. Pat. No. 2,528,378. Other amphoterics such as betaines are also useful in the present composition. Examples of betaines useful herein include the high alkyl betaines such as coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl) carboxy methyl betaine, stearyl bis-(2-hydroxypropyl)carboxymethyl betaine, oleyl dimethyl gamma-carboxypropyl betaine, lauryl bis-(2-hydro-xypropyl)alpha-carboxyet-hyl betaine, etc. The sulfobetaines may be represented by coco dimethyl sulfopropyl betaine, stearyl dimethyl sulfopropyl betaine, amido betaines, amidosulfobetaines, and the like.

Examples of suitable cationic surfactants include stearyldimenthylbenzyl ammonium chloride; dodecyltrimethylammonium chloride; nonylbenzylethyldimethyl ammonium nitrate; tetradecylpyridinium bromide; laurylpyridinium chloride; cetylpyridinium chloride; laurylpyridinium chloride; laurylisoquinolium bromide; ditallow(Hydrogenated) dimethyl ammonium chloride; dilauryldimethyl ammonium chloride; and stearalkonium chloride; and other cationic surfactants known in the art.

Nonionic surfactants useful in this invention can be broadly defined as compounds produced by the condensation of alkylene oxide groups (hydrophilic in nature) with an organic hydrophobic compound, which may be aliphatic or alkyl aromatic in nature.

A preferred synthetic surfactant for use in the present compositions is sodium laureth-3 sulfate. Sodium laureth sulfate tends to provide excellent lathering properties, especially when combined with sodium tripolyphosphate as the inorganic salt in the present compositions.

Cationic Polymers

The present bar compositions can optionally further comprise cationic polymers to improve the lathering and skin feel benefits of the compositions. When present, the present bar compositions will comprise from about 0.001% to about 10%, preferably from about 0.01% to about 5%, more preferably from about 0.05% to about 1%, by weight of the composition, of cationic polymer. Preferred embodiments contain levels of cationic polymer of less than about 0.2%, preferably less than about 0.1%, by weight of the composition. If the level of cationic polymer is too high, the resulting bar composition can exhibit a sticky skin feel.

Suitable cationic polymers for use in the present bar compositions include, but are not limited to, cationic polysaccharides; cationic copolymers of saccharides and synthetic cationic monomers; cationic polyalkylene imines; cationic ethoxy polyalkylene imines; cationic poly[N-[3-(dimethylammonio)propyl]-N'[3-(ethyleneoxyethylene dimethyl ammonio)propyl]urea dichloride]. Suitable cationic polymers generally include polymers having a quaternary ammonium or substituted ammonium ion.

Non-limiting examples of suitable cationic polymers for use herein include cationic hydroxyethyl cellulose (available under the tradename Ucare Polymer JR400®, Ucare Polymer JR-125® or Ucare Polymer LR-400® from Amerchol); cationic starches (available under the tradename STALOK® 100, 200, 300, and 400 from Staley, Inc.); cationic galactomannans based on guar gum (available under the tradename Galactasol® 800 series from Henkel, Inc. and under the tradename JAGUAR® from Meyhall Chemicals, Ltd.). A preferred cationic polymer is guar hydroxypropyl trimonium chloride available from Meyhall Chemicals, Ltd. under the tradename JAGUAR® C13S. Suitable cationic polymers are described in more detail in co-pending U.S. Provisional Application Ser. No. 60/811,545 filed Jun. 6, 2006.

Brightners

Brighteners can be included as optional ingredients in the present compositions at a level of from about 0.001% to about 1%, preferably from about 0.005% to about 0.5%, and more preferably from about 0.01% to about 0.1%, by weight of the composition. Examples of suitable brighteners in the present compositions include disodium4,4'-bis-(2-sulfostyril)-biphenyl (commercially available under the tradename Brightener-49, from Ciba Specialty Chemicals); disodium4,4'-bis-[(4,6-di-anilino-s-triazine-2-yl)-amino]-2,2'-stilbenedisulfonate (commercially available under the tradename Brightener 36, from Ciba Specialty Chemicals); 4,4'-bis-[(4-anilino-6-morpholino-s-triazine-2-yl)-amino]-2,2'-stilbenedi-sulfonate (commercially available under the tradename Brightener 15, from Ciba Specialty Chemicals); and 4,4'-bis-[(4-anilino-6-bis-2(2-hydrox-yethyl)-amino-s-triazine-2-yl)-amino]-2,2'-stilbenedisulfonate (commercially available under the tradename Brightener 3, from Ciba Specialty Chemicals); and mixtures thereof.

Silica

Silica, or silicon dioxide, can be optionally incorporated in the present bar compositions at a level of from about 0.1% to about 15%, preferably from about 1% to about 10%, and more preferably from about 3% to about 7%, by weight of the composition. Silica is available in a variety of different forms include crystalline, amorphous, fumed, precipitated, gel, and colloidal. Preferred forms herein are fumed and/or precipitated silica.

Thickening silica typically has smaller particle size versus normal abrasive silica and is preferred herein. The average particle size of thickening silica is preferably from about 9 μm to about 13 μm, as opposed to normal abrasive silica which has an average particle size of from about 20 μm to about 50 μm. Due to the surface of the preferred thickening silica having a relatively large amount of silinol groups, it can build the water and build the right texture for the present bar compositions. The silinol groups tend to form hydrobondage wherein three-dimensional networks are fabricated to act like a spring in the soap phase to deliver good foaming and good texture. The thickening silica preferably has a high oil absorbency value (DBP), normally indicating porosity and large surface area, and is preferably greater than about 250 (g/100 g), and more preferably greater than about 300 (g/100 g).

Non-limiting examples of suitable thickening silica include: SIDENT 22S commercially available from Degussa; ZEODENT 165 commercially available from J. M. Huber Corp.; SORBOSIL TC15 commercially available from Ineos Silicas; TIXOSIL 43 commercially available from Rhodia; and SYLOX 15X commercially available from W. R. Grace Davidson.

Other optional ingredients in the present bar compositions include: perfumes; sequestering agents, such as tetrasodium ethylenediaminetetraacetate (EDTA), EHDP or mixtures thereof typically in an amount of 0.01 to 1%, preferably 0.01 to 0.05%, by weight of the composition; and coloring agents, opacifiers and pearlizers such as titanium dioxide; all of which are useful in enhancing the appearance or cosmetic properties of the product.

The pH of a 1% solution of the bar composition of the present invention dissolved in water is typically from about 7 to about 12, preferably from about 8 to about 11, and more preferably from about 9 to about 10.

The appearance of the bar composition according to the present invention can be transparent, translucent, or opaque. In one embodiment, the bar composition is opaque.

Although borate compounds can be incorporated in the present compositions, such as those disclosed in U.S. Pat. No. 6,440,908, the present bar compositions preferably do not contain a borate compound. In one embodiment, the present bar composition is free of a borate compound.

The cleansing bar compositions of the present invention can be used by consumers to cleanse skin during bathing or washing.

Process of Manufacture

The bar composition of the present invention can be made via a number of different processes known in the art. Preferably, the present compositions are made via a milling process, resulting in milled bar compositions.

A typical milling process of manufacturing a bar composition includes: (a) a crutching step in which the soap is made, (b) a vacuum drying step in which the soap is made into soap noodles, (c) an amalgamating step in which the soap noodles are combined with other ingredients of the bar composition, (d) a milling step in which a relatively homogeneous mixture is obtained, (e) a plodding step in which the soap mixture is extruded as soap logs and then cut into soap plugs, and (f) a stamping step in which the soap plugs are stamped to yield the finished bar soap composition.

Water Activity Test Method

Water Activity ("Aw") is a measurement of the energy status of the water in a system. It indicates how tightly water is bound, structurally or chemically, within a composition. Water activity ("Aw") is defined as the ratio of the water vapor pressure over a sample (P) to that over pure water ($P_0$):

$$Aw=P/P_0$$

The chilled-mirror dewpoint technique can be used to measure the Aw of a sample. The sample is equilibrated with the headspace of a sealed chamber that contains a mirror and a means of detecting condensation on the mirror. At equilibrium, the relative humidity of the air in the chamber is the same as the water activity of the sample. A beam of light is directed onto the mirror and reflected into a photodetector cell. The photodetector senses the change in reflectance when condensation occurs on the mirror. A thermocouple attached to the mirror then records the temperature at which condensation occurs.

For purposes of the present invention, the Aw of a bar composition can be measured using the AquaLab Series 3 Water Activity Meter available from Decagon Devices, Inc. of Pullman, Washington USA. The following procedure is utilized to determine the Aw of a bar composition using the AquaLab Series 3 Water Activity Meter:

1. Check the sample container of the meter to make sure it is clean and dry before the test;
2. Cut a bar soap sample into 0.2 to 0.4 cm thick pieces with stainless knife;
3. Put samples into the container of the meter to a ⅓" to ½" depth;
4. Press the sample with a gloved finger lightly to make sure the bottom of the container is covered by the sample;
5. Put the sample container back into the sample cabinet of the meter and cover it, and turn dial to activate the meter;
6. Wait for the equilibrium until a green LED flashing and/or beeps; and
7. Record the test temperature and Aw of the sample.

EXAMPLES

The following are non-limiting examples of the cleansing bar compositions of the present invention. Amounts of each ingredient are approximate weight percentages by weight of the bar composition.

| Ingredient | Example 1 | Example 2 | Example 3 | Example 4 |
|---|---|---|---|---|
| Soap Noodle[a] | 58.00% | 58.00% | 58.00% | 58.00% |
| Raw Corn Starch | 12.09% | 8.76% | 6.54% | 3.20% |
| Magnesium Sulfate | — | 3.00% | 5.00% | 8.00% |
| Dye Solution | 0.50% | 0.02% | 0.02% | 0.02% |
| Perfume | 0.90% | 0.90% | 0.90% | 0.90% |
| Sodium Tripolyphosphate | 2.50% | 2.50% | 2.50% | 2.50% |
| Titanium Dioxide | 0.50% | 0.50% | 0.50% | 0.50% |
| Palm Kernel Fatty Acid | 0.75% | 0.75% | 0.75% | 0.75% |
| Approximate Water Lost During Processing | (1%) | (1%) | (1%) | (1%) |
| Approximate Water Content in Finished Product | 20-25% | 20-25% | 20-25% | 20-25% |

| Ingredient | Example 5 | Example 6 | Example 7 | Example 8 |
|---|---|---|---|---|
| Soap Noodle[a] | 58.00% | 58.00% | 54.00% | 54.00% |
| Raw Corn Starch | 3.54% | 4.50% | 9.25% | 9.25% |
| Magnesium Sulfate | 8.00% | — | — | — |
| Tetrasodium Pyrophosphate | — | 8.00% | 8.00% | 8.00% |
| Dye Solution | 0.50% | 0.50% | 0.50% | 0.50% |
| Perfume | 0.90% | 0.90% | 0.90% | 0.90% |
| Sodium Tripolyphosphate | 2.50% | 2.50% | 2.50% | 2.50% |
| Titanium Dioxide | 0.50% | 0.50% | 0.50% | 0.50% |
| Palm Kernel Fatty Acid | 0.75% | 0.75% | 1.50% | 0.75% |
| Sodium Laureth 3 Sulfate | — | — | — | 0.75% |
| Approximate Water Lost During Processing | (1%) | (1%) | (1%) | (1%) |
| Approximate Water Content in Finished Product | 20-25% | 20-25% | 20-25% | 20-25% |

| Ingredient | Example 9 | Example 10 | Example 11 | Example 12 |
|---|---|---|---|---|
| Soap Noodle[a] | 58.00% | 58.00% | 54.00% | 54.00% |
| Glycerin | — | — | 3.00% | 3.00% |
| Raw Corn Starch | — | 12.50% | 17.00% | 12.50% |

-continued

| | | | | |
|---|---|---|---|---|
| Tetrasodium Pyrophosphate | 8.00% | — | — | 3.00% |
| Brightener | 0.02% | 0.02% | — | — |
| Perfume | 0.90% | 1.20% | 1.40% | 1.40% |
| Sodium Tripolyphosphate | 2.50% | 2.50% | 2.50% | — |
| Titanium Dioxide | 0.50% | 0.50% | 0.50% | 0.50% |
| Palm Kernel Fatty Acid | 0.75% | 0.75% | — | — |
| Sodium Lauryl Sulfate | — | — | 0.10% | 0.10% |
| Pregelatinized Starch[b] | 4.50% | — | — | — |
| Trichlorocarban | — | — | 0.60% | 0.60% |
| Dye Solution | 0.50% | 0.50% | 0.50% | 0.50% |
| Approximate Water Lost During Processing | (1%) | (1%) | (1%) | (1%) |
| Approximate Water Content in Finished Product | 20-25% | 20-25% | 20-25% | 20-25% |

[a]The Soap Noodle utilized in these examples has the following approximate composition: about 85% Anhydrous Soap (50% Tallow/30% Palm Oil Stearine/20% Palm Kernel Oil (or 20% Coconut Oil)), about 0.2% Free Citric Acid, about 0.2% Sodium Citrate, about 0.05% Tetrasodium DPTA, about 0.05% Tetrasodium HEDP, about 0.6% Sodium Chloride, about 1% Glycerin, and from about 12% to about 18% Water, the balance being unsaponifiables. These percentage amounts are by weight of the Soap Noodle.

[b]Pregelatinized starch is available as PREGEL-A M 0300 from Tianjin Tingfung Starch Development Co., Ltd. of Tianjin, China.

In these examples, the Soap Noodles are made via a conventional process involving a crutching step and a vacuum drying step. The Soap Noodles are then added to an amalgamator. The ingredients of perfume, brightener, and titanium dioxide are then added to the amalgamator and mixed for about 10 to 15 seconds. The ingredients such as water, inorganic salts (such as sodium tripolyphosphate, tetrasodium pyrophosphate, and/or magnesium sulfate), free fatty acid (such as palm kernel fatty acid), carbohydrate structurant (such as raw starch or pregelatinized starch), dye solution, and trichlorocarban are then added to the amalgamator and then mixed for about 30 to 45 seconds. This soap mixture is then processed through conventional milling, plodding, and stamping steps to yield the finished bar soap compositions.

The dimensions and values disclosed herein are not to be understood as being strictly limited to the exact numerical values recited. Instead, unless otherwise specified, each such dimension or value is intended to mean both the recited value and a functionally equivalent range surrounding that value. For example, a dimension disclosed as “40 mm” is intended to mean “about 40 mm”.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A cleansing bar composition comprising:

(a) at least about 15%, by weight of said composition, of water;

(b) from about 40% to about 84%, by weight of said composition, of soap;

(c) from 5.5% to about 15%, by weight of said composition, of an inorganic salt comprising a mixture of magnesium sulfate and sodium tripolyphosphate or a mixture of tetrasodium pyrophosphate and sodium tripolyphosphate; and (d) a component selected from the group consisting of:

(i) carbohydrate structurant;

(ii) humectant;

(iii) free fatty acid;

(iv) synthetic surfactant; and (v) mixtures thereof wherein a 1% solution of the cleansing bar dissolved in water has a pH from about 7 to about 12;

wherein said cleansing bar composition has a Water Activity (Aw) of less than about 0.95; and wherein said cleansing bar composition is a milled bar.

2. The cleansing bar composition of claim 1, wherein said inorganic salt comprises about 10.5% by weight of said composition.

3. The cleansing bar composition of claim 1, wherein said cleansing bar composition comprises at least about 20%, by weight of said composition, of water.

4. The cleansing bar composition of claim 1, wherein said carbohydrate structurant is selected from the group consisting of raw starch, pregelatinized starch, and mixtures thereof.

5. The cleansing bar composition of claim 4, wherein said carbohydrate structurant is present at a level of from about 1% to about 20%, by weight of said composition.

6. The cleansing bar composition of claim 1, wherein said humectant is selected from the group consisting of polyhydric alcohols, water soluble alkoxylated nonionic polymers, and mixtures thereof.

7. The cleansing bar composition of claim 6, wherein said humectant is present at a level of from about 0.1% to about 20%, by weight of the composition.

8. The cleansing bar composition of claim 6, wherein said humectant is a polyhydric alcohol selected from the group consisting of glycerin, sorbitol, and mixtures thereof.

9. The cleansing bar composition of claim 1, wherein said free fatty acid is selected from the group consisting of tallow fatty acid, coconut fatty acid, palm fatty acid, and palm kernel fatty acid.

10. The cleansing bar composition of claim 9, wherein said free fatty acid is present at a level of from about 0.01% to about 10%, by weight of said composition.

11. The cleansing bar composition of claim 9, wherein said free fatty acid is palm kernel fatty acid.

12. The cleansing bar composition of claim 1, wherein said synthetic surfactant is selected from the group consisting of anionic surfactants, amphoteric surfactants, nonionic surfactants, zwitterionic surfactants, cationic surfactants, and mixtures thereof.

13. The cleansing bar composition of claim 12, wherein said synthetic surfactant is present at a level of from about 0.1% to about 20%, by weight of said composition.

14. The cleansing bar composition of claim 12, wherein said synthetic surfactant is sodium laureth sulfate.

15. The cleansing bar composition of claim 1, wherein said Water Activity (Aw) of said cleansing bar composition is less than about 0.90.

16. The cleansing bar composition of claim 1, wherein said Water Activity (Aw) of said cleansing bar composition is less than about 0.85.

17. The cleansing bar composition of claim 1, wherein said cleansing bar composition is opaque.

18. The cleansing bar composition of claim 17, wherein said cleansing bar further comprises titanium dioxide.

19. A method of cleansing skin comprising the step of contacting said skin with a cleansing bar composition according to claim 1.

* * * * *